United States Patent
van der Plaats et al.

(10) Patent No.: US 6,203,760 B1
(45) Date of Patent: Mar. 20, 2001

(54) AUTOSAMPLER HAVING GRIPPER WITH SHAPE MEMORY METAL ACTUATOR

(75) Inventors: Gosse van der Plaats, Beringen (BE); Eric Quaedackers; Peter Theunissen, both of Maastricht (NL)

(73) Assignee: PerkinElmer Instruments LLC, Norwalk, CT (US)

( * ) Notice: Subject to any disclaimer, the term of this patent is extended or adjusted under 35 U.S.C. 154(b) by 0 days.

(21) Appl. No.: 09/250,053

(22) Filed: Feb. 12, 1999

(51) Int. Cl.$^7$ .................................................. B01L 9/00
(52) U.S. Cl. .............................. 422/104; 422/63; 422/64; 422/99; 436/43
(58) Field of Search ................................ 422/63, 64, 65, 422/103, 104; 436/43, 47, 147

(56) References Cited

U.S. PATENT DOCUMENTS

| | | | |
|---|---|---|---|
| 4,476,733 | 10/1984 | Chlosta et al. | 73/863.91 |
| 4,670,219 | 6/1987 | Nelson et al. | 422/63 |
| 4,816,730 | 3/1989 | Wilhelm et al. | 318/568 |
| 4,874,250 | 10/1989 | Gonner | 374/43 |
| 5,198,066 | * 3/1993 | Cederstrom | 156/538 |
| 5,235,862 | 8/1993 | Harada | 73/863.11 |
| 5,398,556 | 3/1995 | Lang | 73/863.11 |
| 5,472,669 | * 12/1995 | Miki et al. | 422/63 |
| 5,665,309 | * 9/1997 | Champseix et al. | 422/63 |
| 5,766,021 | * 6/1998 | Pickles et al. | 439/70 |
| 5,779,133 | * 7/1998 | Jackson et al. | 228/13 |

FOREIGN PATENT DOCUMENTS 3814959 11/1989 (DE).

OTHER PUBLICATIONS

SSC5200 Series—Comprehensive Brochure on Thermal Analysis Systems—Seiko Instruments, Inc., 4 of 16 pages, published by 1993.

* cited by examiner

Primary Examiner—Arlen Soderquist
Assistant Examiner—Dwayne K. Handy
(74) Attorney, Agent, or Firm—St. Onge Steward Johnston & Reens LLC (57) ABSTRACT

An autosampler for manipulating a specimen container is disclosed. At least one specimen container tray, having a plurality of recesses for receiving a specimen container, is removably fixed to a ground plate. A specimen container manipulating device is positioned on top of the ground plate and adjacent to the specimen container tray. The specimen container manipulating device comprises a gripper comprising a gripper housing and a plurality of gripping fingers extending distally from the gripper housing. The gripping fingers are held in place by a member which is movable inside the gripper housing between an upper and lower position. The gripping fingers are movable between an open and closed position, such that, when in the closed position, the gripping fingers grip and hold the specimen container. Shape memory metal is positioned inside the gripper housing and connected to the movable member for controlling movement of the gripping fingers between the open and closed positions. When heat, such as voltage, is applied to the shape memory metal, it causes the temperature of the shape memory metal to rise, causing the metal to undergo a phase transition and constrict. When the shape memory metal constricts, it moves the movable member from the lower position to the upper position, causing the gripping fingers to move from the closed position to the open position.

15 Claims, 10 Drawing Sheets

AUTOSAMPLER HAVING GRIPPER WITH SHAPE MEMORY METAL ACTUATOR

FIELD OF THE INVENTION

The present invention relates to an automatic sampling device and, in particular, to a device that automatically transfers a sample container from a sample tray into and out of known laboratory analyzing equipment, for the examination of, for example, the heats of transformation of a sample.

BACKGROUND OF THE INVENTION

It is known to use differential scanning calorimeters (DSC) and thermal gravimetric analysis (TGA) machines to conduct thermal analyses of selected samples in order to examine certain characteristics of the samples as a function of temperature. Sometimes it is necessary to carry out measurements on a large number of samples; therefore, it is desirable and known in the art to mechanize the manipulation of the specimens, which is commonly referred to as autosampling.

One autosampler is shown in U.S. Pat No. 5,398,556 to Lang. Lang discloses a device comprising a vertical gripper member and a rotatable specimen plate for holding a plurality of specimen containers. The specimen container is transferred to the measuring location in the parent machine (such as the DSC or TGA) by rotating the specimen plate so that the desired specimen container is positioned under the gripper. Then, the gripper, which is driven by a motor, is lowered and gripping fingers attached to a gripping member grip the specimen container. The container is then raised from the specimen plate by raising the gripping member. The specimen plated is then rotated until a recess in the specimen plate is located underneath the gripping member. Next, the gripping member is lowered through the recess in the specimen plate and places the specimen container at the measuring location, which is directly underneath the gripper. The specimen container is then deposited on the measuring location by releasing the gripper fingers.

The gripper taught by the Lang patent is driven by two different drive motors and a cam mechanism; it is particularly disadvantageous in that the gripping motion itself is driven by a motor. As such, the gripper device taught by the Lang '556 is rather complicated in that it has many moving parts and if the motor over- or under-drives the gripper, then an error could occur in the placement of the sample. The device is further undesirable because the sample tray table rotates. A user must wait until the end of the sample run before the sample tray table can be removed and reloaded with additional samples.

What is desired, therefore, is an autosampler which does not require many moving parts, has a gripper wherein the gripping action is not driven by a motor, has a fixed sample tray table and which has a sample tray table that may be at least partially reloaded while the parent machine is conducting an analysis of selected samples.

SUMMARY OF THE INVENTION

Accordingly, it is an object of the present invention to provide an autosampler which has a relatively few number of moving parts when compared to conventional autosamplers.

It is another object of the present invention to provide an autosampler which eliminates the need for a drive motor to operate the gripping and releasing action of the gripping mechanism.

It is still another object of the present invention to provide an autosampler which has a fixed sample tray table.

It is yet a further object of the present invention to provide an autosampler which has a sample tray table which can be at least partially reloaded or unloaded while the parent machine is conducting an analysis of selected specimens.

It is still another object of the present invention to provide an autosampler which can fit onto an existing cover of conventional parent machines with little or no retooling and which does not increase the footprint of the parent machine.

It is still a further object of the present invention to provide an autosampler which is extremely reliable, easy to use, lightweight, and cost-effective to manufacture and maintain.

To overcome the deficiencies of the prior art and to achieve the objects and advantages listed above, an autosampler is disclosed which comprises: a ground plate; at least one specimen container tray removably fixed to the ground plate; and a specimen container manipulating device, positioned on top of the ground plate and adjacent to the specimen container tray.

The specimen container manipulating device comprises a gripper having an elongated gripper housing. A movable member, such as a spool, is positioned inside the gripper housing and is movable between an upper and a lower position. The spool has a plurality of grooves substantially equidistantly spaced from each other which extend along the outside of the spool; a rod is removably connected to the spool.

A plurality of gripping fingers protrudes from the distal end of the gripper and move between an open and closed position. Each gripping finger is positioned in a groove of the spool. In the closed position, the gripping fingers can grip, hold and transfer a specimen container; in the open position, the gripping fingers release the specimen container.

Shape memory metal is positioned inside the gripper housing and around the rod. When heat, such as voltage, is applied to the shape memory metal, it causes the temperature of the metal to rise; the metal then undergoes a phase transformation and shrinks or constricts. When the metal shrinks, it pulls up on the rod, raising the spool from the lower position to the upper position. When the spool moves to the upper position, it causes the gripping fingers to move from the closed position to an open position.

The autosampler may further comprise at least two specimen container trays, which are stationary while the gripper manipulates the specimen containers located thereon. Advantageously, while the gripper is manipulating containers on one tray, the operator may load or unload the other sample tray. This saves time because the operator does not have to wait until the autosampler is finished with all of the samples before loading additional samples or unloading spent samples.

The invention and its particular features and advantages will become more apparent from the following detailed description when considered with reference to the accompanying drawings.

BRIEF DESCRIPTION OF THE DRAWINGS

FIG. 4 shows the spool in the lowermost position and the gripping fingers closed;

FIG. 4A shows the spool between the upper and lower positions and the gripping fingers between the open and closed position (only two gripping fingers shown for convenience); and FIG. 4B shows the spool in the upper position and the gripping fingers in the open position (only two gripping fingers shown for convenience);

DETAILED DESCRIPTION OF THE DRAWINGS

Referring to the drawings in detail, an autosampler is shown and generally designated by the reference numeral 10. It should be noted that for the sake of clarity not all of the components and parts of autosampler 10 may be shown and/or marked in all the drawings. As used in this description, the terms "up", "down", "top", "bottom", etc., refer to autosampler 10 when in the orientation illustrated in FIG. 1.

Figure 1:
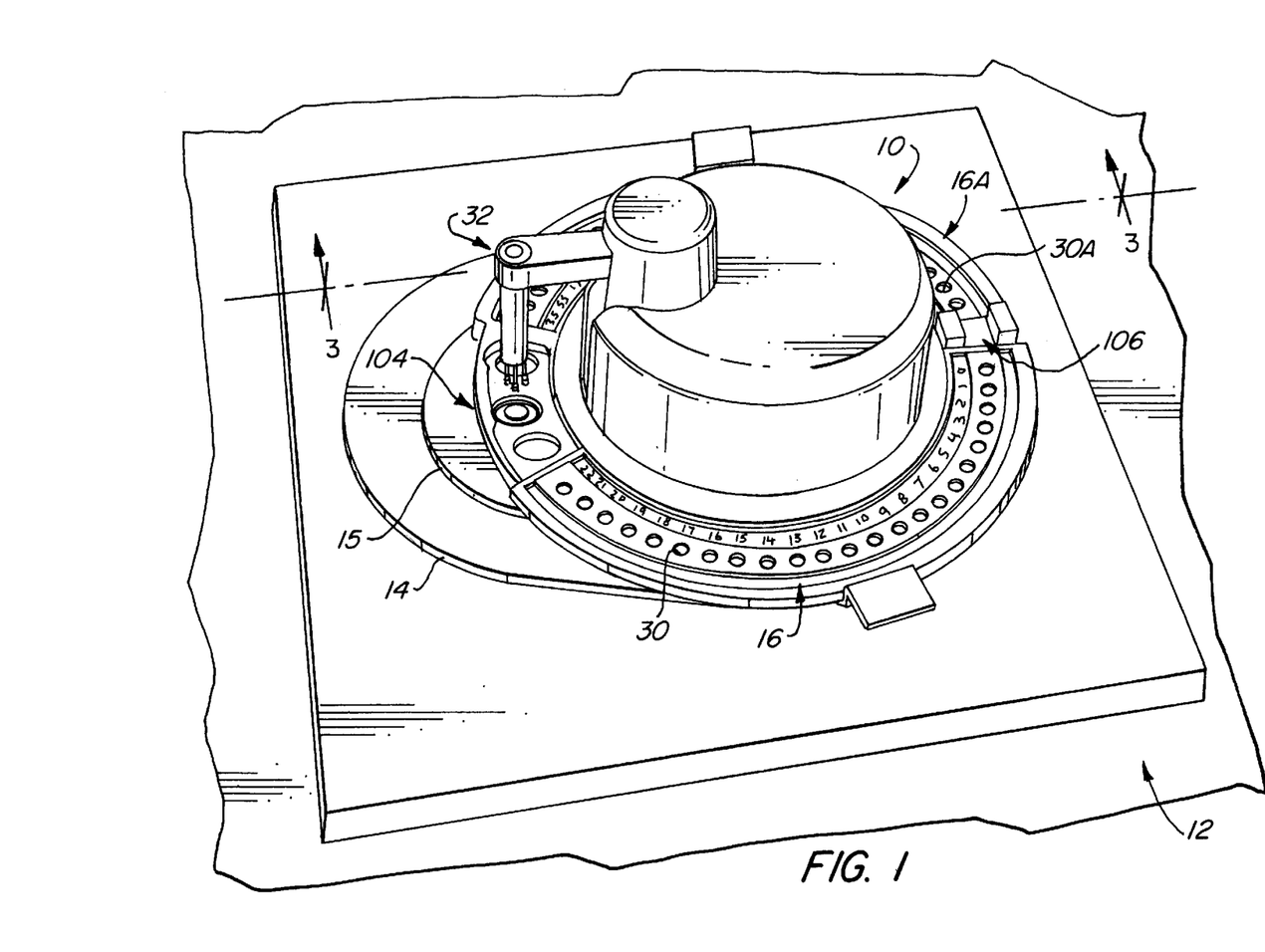
FIG. 1 is a top perspective view of an autosampler and removable cover, constructed in accordance with the present invention.

Referring now more particularly to FIG. 1, autosampler 10 is designed to be used with a parent instrument 12, for example, a differential scanning calorimeter (DSC) or a thermal gravimetric analysis (TGA) machine. As is known, DSC or TGA machines conduct thermal analyses of selected samples in order to examine certain characteristics of the samples as a function of temperature. It should be understood that autosampler 10 may be used with other analytical instruments known in the art, after obvious modifications that will become apparent after reading this description. Discussion herein has been limited to DSC and TGA machines for convenience only and is not intended to be limiting.

Before operations begin, operational data can be provided to a computer (not shown) of the autosampler 10 by an operator through a keyboard (not shown) with a display means (not shown) both of which are known in the art. Or, the computer of the autosampler 10 may be driven by a computer program provided by a host computer (not shown), such as the one marketed by Perkin-Elmer Corporation, known in the field by the trademark Pyris™.

As best shown in FIGS. 1–3, 5, 6, autosampler 10 generally comprises: a base plate 14; a ground plate 15 connected to the base plate 14; at least one specimen container tray 16 removably fixed to the ground plate 15; and a specimen container manipulating device 18, positioned on top of the ground plate 15 and adjacent to the specimen container tray 16 for manipulating specimen container 20.

Base plate 14 may be made of any suitable material but is preferably made of aluminum and may be made in any suitable fashion so long as it suitably connects manipulating device 18 to parent instrument 12 (FIG. 1). The base plate 14 shown in FIG. 5 shows one embodiment for connecting manipulating device 18 to the parent instrument 12, which in this case is a TGA, and FIG. 6 illustrates another embodiment of base plate 14A for connecting the manipulating device 18 to the parent instrument 12, which in this case is a DSC.

Figure 3:
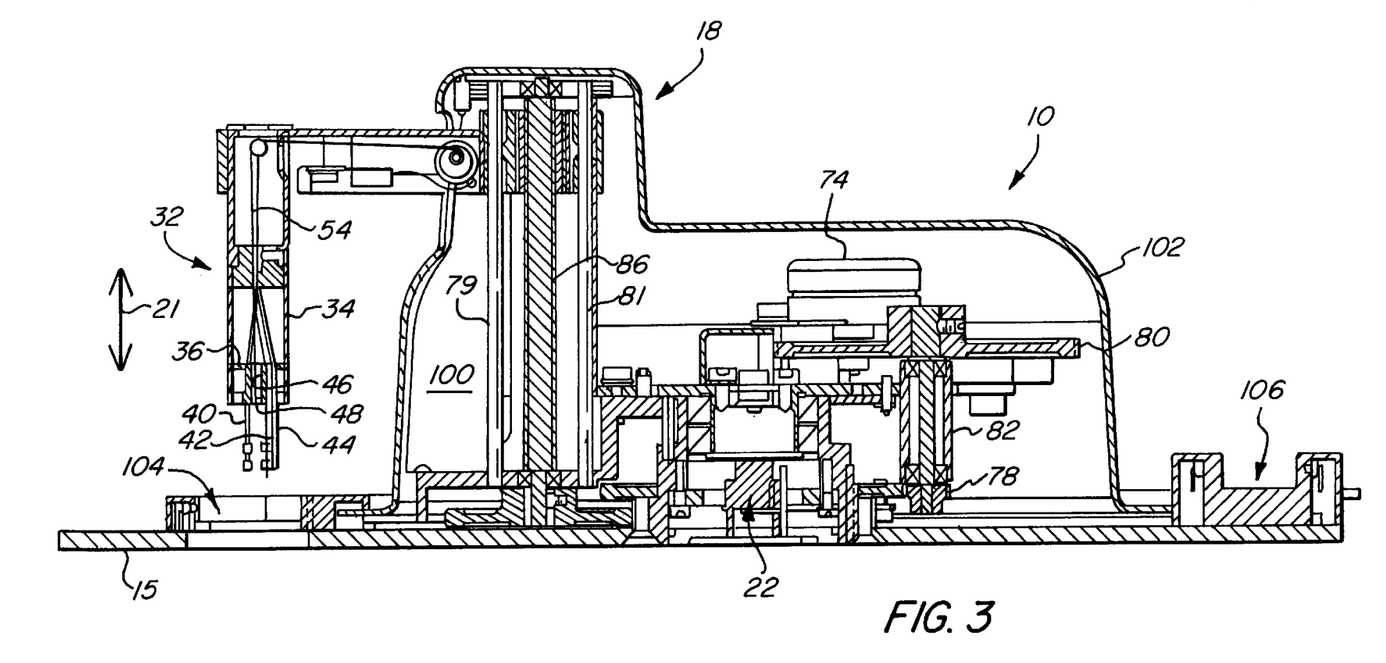
FIG. 3 is a cross-sectional view of the autosampler, taken along line 3—3 of FIG. 1, showing the gripper fingers in the closed position.
Figure 5:
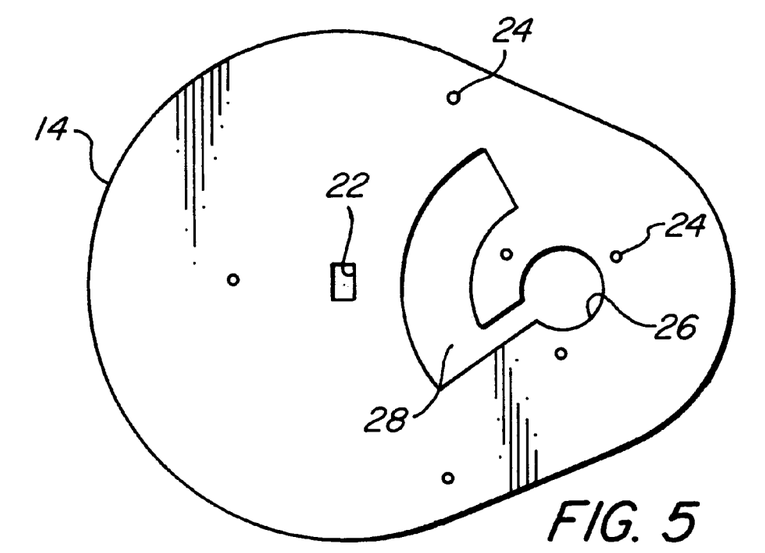
FIG. 5 is a top view of a base plate.
Figure 6:
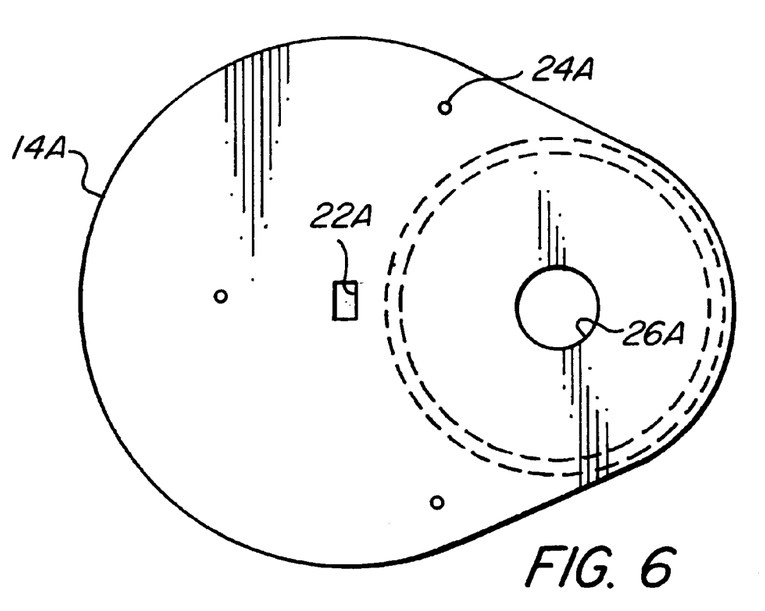
FIG. 6 is a top view of an alternative embodiment of the base plate shown in FIG. 5.

Referring in detail to FIGS. 3, 5, 6, base plates 14, 14A have connectors 22, 22A, respectively, for connecting parent instrument 12 to manipulating device 18. Base plates 14, 14A each have a plurality of mounting holes such as 24, 24A through which conventional screws may be inserted for mounting base plates 14, 14A to the parent instrument 12 (FIG. 1). Base plates 14, 14A each have furnace access holes 26, 26A through which specimen container 20 (FIGS. 7, 8) is dropped into the parent instrument 12 so that container 20 may be heated to a predetermined temperature for analysis. Base plate 14 additionally comprises thermocouple access 28.

Figure 2:
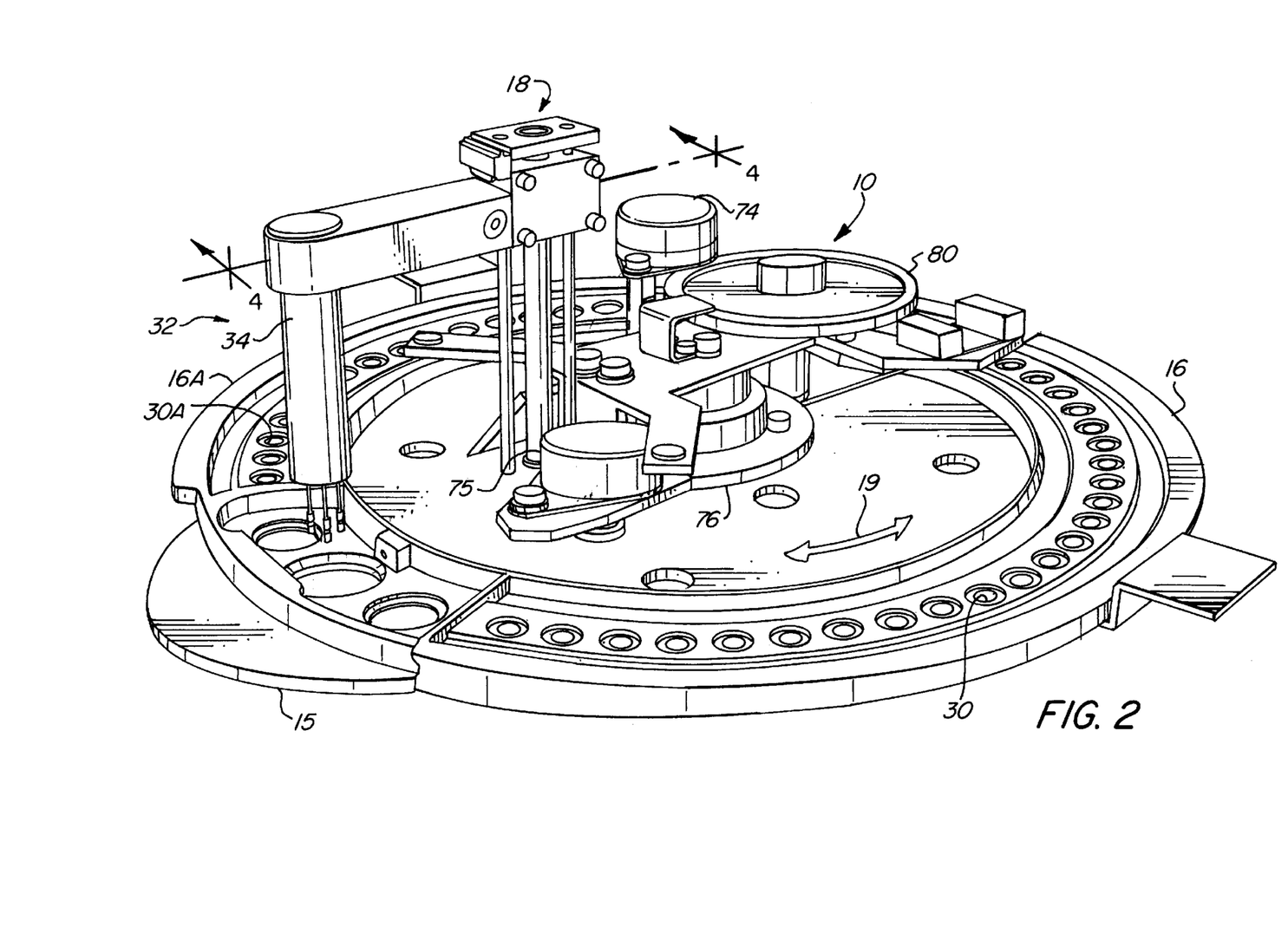
FIG. 2 is a perspective view of the autosampler shown in FIG. 1, with the shield and cover removed for clarity.
Figure 7:
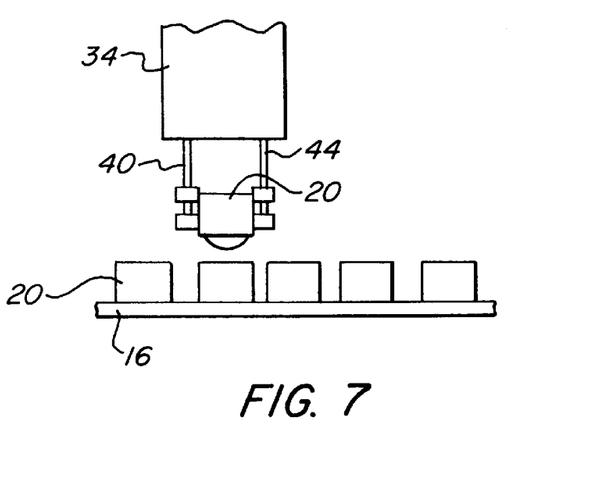
FIG. 7 is a side plan view of the gripper gripping a specimen container, only two gripper fingers shown for the sake of clarity.
Figure 8:
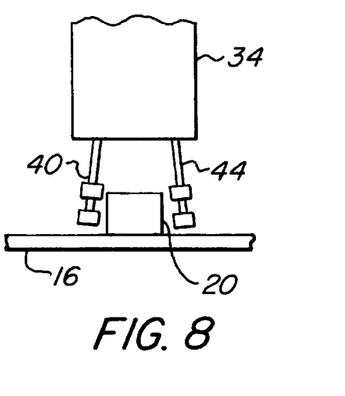
FIG. 8 is a side plan view of the gripper in the open position about a specimen container, only two gripper fingers shown for the sake of clarity.
Figure 9:
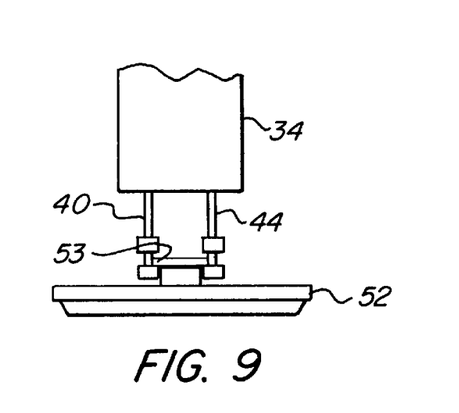
FIG. 9 is a side plan view of the gripper, illustrating a lip of a furnace lid being gripped by the gripper fingers, only two gripper fingers shown for the sake of clarity.

Referring to FIGS. 1, 2, autosampling device 10 further comprises at least one specimen container tray 16 which is removably fixed to ground plate 15 and has a plurality of recesses 30, 30A for receiving a specimen container 20 (FIGS. 7, 8). In the preferred embodiment, autosampler 10 comprises two sample trays 16, 16A. Advantageously, trays 16, 16A are designed to hold a unique number of sample containers 20. For example, tray 16 may hold twenty-two sample containers 20 and tray 16A may hold twenty-three sample containers 20. This feature helps to ensure that the operator does not mistakenly place tray 16 in the location of tray 16A and vice versa. Each recess 30, 30A of tray 16, 16A is labeled with a unique identifying number (FIG. 1) for easy sample identification.

Figure 11:
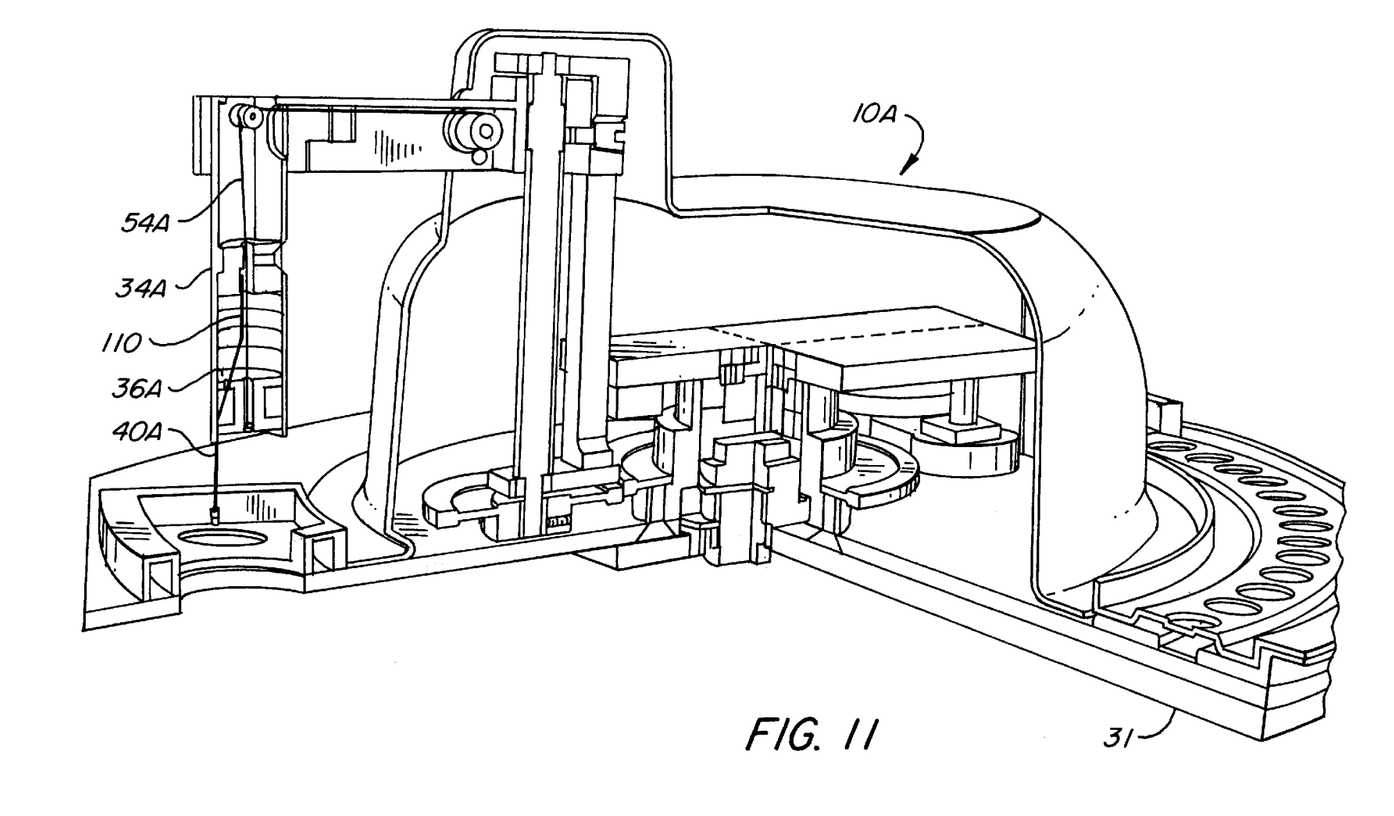
FIG. 11 is a side view of the autosampler shown in FIG. 1 with parts broken away and showing an alternative embodiment of the gripper design.

Additionally, trays 16, 16A each have a top and bottom and recesses on the bottom there of to receive at least one positioning pin 31, (FIG. 11). The positioning pins 31 are formed in the ground plate 15. The positioning pins for positioning tray 16 are located in different places than those for positioning tray 16A, which prevents tray 16 from being inserted into the location of tray 16A and vice-versa.

Autosampler 10 comprises specimen container manipulating device 18, which is best shown in FIGS. 2, 3. Manipulating device 18 moves in two directions: in a rotational manner shown by arrow 19 (FIG. 2) and in a vertical direction shown by arrow 21 (FIG. 3). Movement in these two directions allows manipulating device 18 to access each container 20, transfer it from the specimen tray 16, 16A through furnace access hole 26, 26A of base plate 14, 14A to the furnace of the parent machine 12, and return it to its appropriate position on the sample tray 16, 16A. Movement in these two directions also allows gripper 32 a sufficient range of motions to access furnace lid 52 and move it onto and off of the furnace access hole, as desired.

Figure 4:
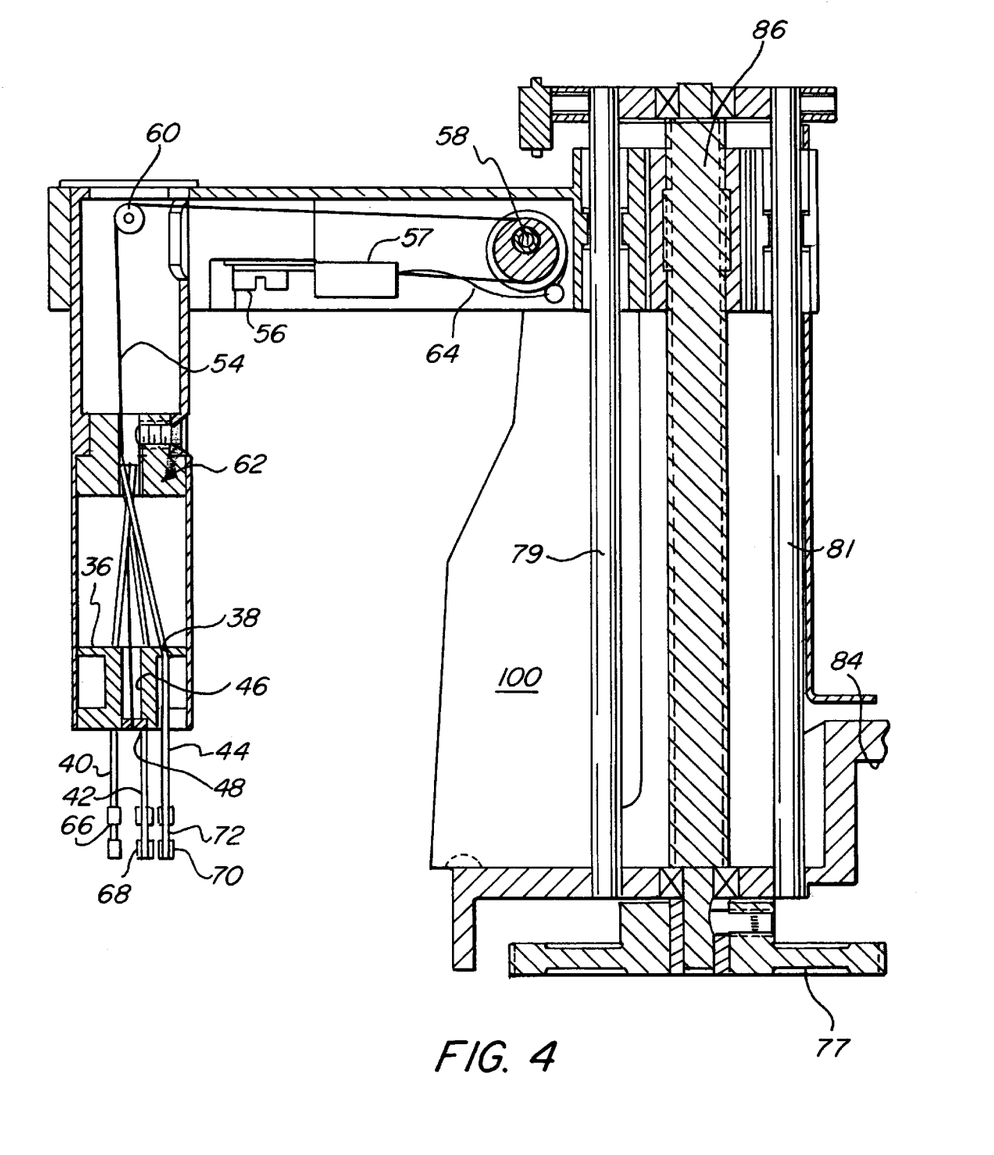
FIGS. 4, 4A and 4B are enlarged cross-sectional views of the gripping device, taken along line 4—4 of FIG. 2 showing the operation of a spool and gripping fingers.

Referring to FIGS. 3, 4, specimen container manipulating device 18 comprises a gripper 32 having an elongated gripper housing 34. A movable member 36, such as a spool, is positioned inside the gripper housing 34 and is movable between an upper position (FIG. 4B) and lower position (FIGS. 3, 4). Gripper 32 further comprises gripper fingers 40, 42, 44 which extend distally from one end of gripper housing 34.

Spool 36 has a plurality of grooves such as 38 which are spaced from each other and extend from the top of spool 36 to its bottom on the outside thereof. Preferably, grooves 38 are substantially equidistantly spaced about spool 36. Grooves 38 hold gripping fingers 40, 42, 44 in place and keep them equidistantly spaced from each other. In the most preferred embodiment, grooves 38 and fingers 40, 42, 44 are about 120° apart. It should be understood that the number of grooves 38 in spool 36 preferably corresponds to the number of gripping fingers desired. It should be further understood that the number of grooves 38 and the number of gripping fingers, such as 40, could vary, depending on the user's needs.

Spool 36 also comprises a rod member 48. Rod 48 may be made of any suitable material but is preferably made of a material that does not absorb heat, such as nylon. Spool 36 is rendered substantially hollow by a bore 46 which extends therethrough. A recessed portion at the bottom of spool 36 forms a shoulder thereon and is sized and shaped for receiving rod 48. It should be understood, however, that spool 36 may be designed in any manner so long as it holds gripping fingers in position and is movable between an upper and lower position in a smooth and steady manner.

As noted and as best shown in FIGS. 3, 4, 4A, 4B, 7–9, gripper 32 comprises a plurality of gripping fingers 40, 42, 44 (each finger may not be shown in all the drawings). Each gripping finger 40, 42, 44 is positioned in a groove 38 of spool 36 and protrudes from the distal end of the gripper housing 34. The gripping fingers 40, 42, 44 are movable between an open position (FIGS. 4B, 8) and closed position (FIGS. 3, 4, 7, 9) for gripping and releasing the specimen container 20 or furnace lid 52.

Fixed member 62 is positioned inside gripper housing 34 and between spool 36 and the top of gripper 32. Fixed member 62 receives the top of gripper fingers 40, 42, 44 and keeps then aligned properly during operation. Fixed member 62 may be made of any suitable material, but is preferably made of aluminum.

Shape memory metal wire 54 is used to move spool 36 between the upper and lower positions. Any suitable shape memory metal may be used; in the preferred embodiment, the metal contains a nickel-titanium alloy. Shape memory metal 54 is marketed by UMS (Usines Metallurgiques Suisses). Shape memory metal 54, in its most preferred embodiment, has a diameter of about 0.15 mm.

Figure 4A:
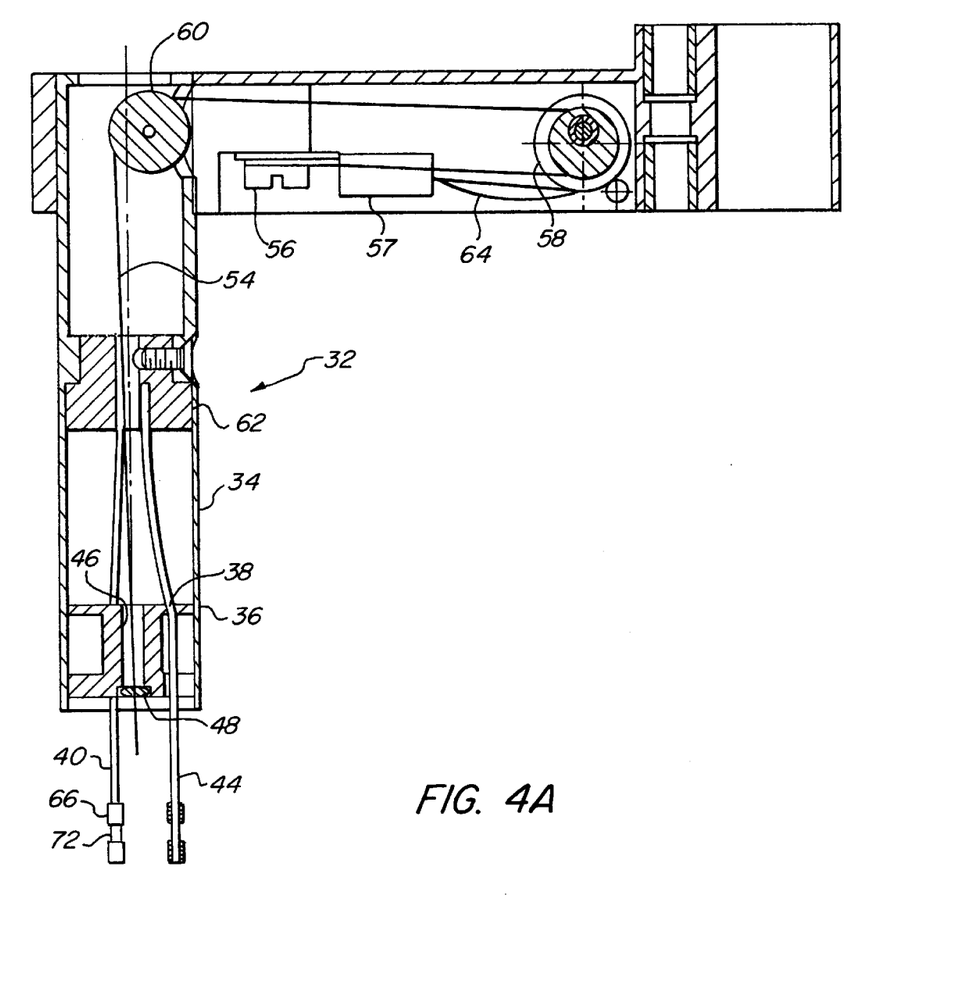
Figure 4B:
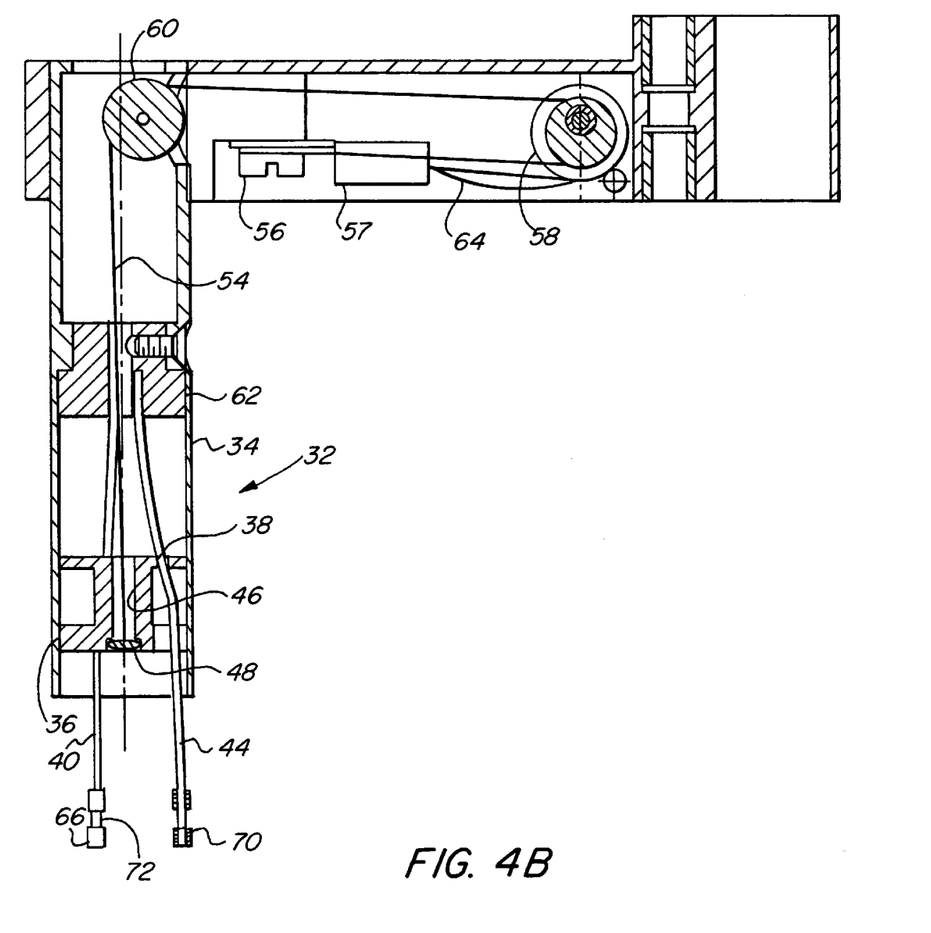

As best shown in FIGS. 4, 4A, 4B, shape memory metal 54 is positioned inside gripper housing 34 and actuates spool 36. It should be understood that wire 54 may be configured in any suitable manner so as to actuate spool 36, the embodiment shown and described being the most preferred.

Wire 54 is arranged in gripper housing 32 as follows. Wire 54 starts at screw 56, extends under a metal plate (not shown) at terminal block 57, wraps around eccentric screw 58, then roller 60 (which is preferably made of Teflon), through a channel of fixed member 62, around rod 48 positioned at the bottom of spool 36 and then back up through gripper housing 34, around spool 60 and roller 58, terminating at screw 56. Tension on wire 54 is adjusted by rotating eccentric screw 58, which is preferably accomplished at the factory.

A voltage source (not shown), which is commonly known in the art, is connected to electrical connection wire 64 for applying a predetermined amount of voltage to the shape memory metal wire 54 at 56. In a preferred embodiment, an operator applies about four volts to the wire 54. When voltage is applied to the shape memory metal 54 through electrical connection 64, the shape memory metal 54 heats up and undergoes a phase transition causing the wire 54 to constrict or shrink. When wire 54 shrinks, it causes the spool 36 to move from the lower position (FIG. 4), upward through gripper housing 34 (FIG. 4A) to the upper position (FIG. 4B). Movement of spool 36 to the upper position moves the gripping fingers 40, 42, 44 from the closed position (FIG. 4) to the open position (FIGS. 4B, 8).

It should be understood that heating wire 54 via electrical connection is the most convenient and preferred method to effect the desired phase change; however, any suitable means may be used to cause the transformation. Other suitable means for heating wire 54 include, for example, an open flame.

Most preferably, each gripping finger 40, 42, 44 has a bushing 66, 68, 70 (best shown in FIGS. 4, 4A, 4B) affixed, such as by gluing, to the end closest to specimen container 20. Each bushing 66, 68, 70 has a recessed portion, such as 72, therein for receiving a lip 53 of a furnace cover 52. See FIG. 9. Bushings 66, 68, 70 facilitate the manipulation of furnace cover 52 because cover 52 is relatively heavy when compared to container 20. Bushings 66, 68, 70 are unnecessary, however, to manipulate specimen container 20 because container 20 is relatively lightweight; frictional force alone is sufficient to manipulate container 20.

Specimen manipulating device 18 moves in both a rotational direction shown by arrow 19 (FIG. 2) and in a vertical direction shown by arrow 21 (FIG. 3) and from position to position by a plurality of stepper motors 74, 75. It should be understood, however, that any suitable means may be used to move manipulator 18, such as mechanical, hydraulic or magnetic means, or combinations thereof.

Referring to FIGS. 2–4, a conventional stepper motor 74 known in the art rotates the specimen-manipulating device 18 in a horizontal plane. Any suitable stepper motor may be used; a stepper motor marketed under the brand-name AIRPAX and having a serial number M82101-P2 and having the following characteristics is preferred—volts: 12; ohms/coil: 110; deg/step: 7.5°. Fixed gear 76 is fixed to base plate 12. Orbital gears 78, 80, connected via shaft 82 therebetween, turn about fixed gear 76. Connecting member 84 connects gripper housing 34 to shaft 82 to effect rotational movement of the gripper 32.

Gripper 32 moves in a vertical direction via precision lead screw 86. Vertical movement of gripper 32 is driven by a motor 75 having the same operational characteristics as motor 74. Motor 75 drives gear wheel 77, which is connected to lead screw 86. Lead screw 86 cooperates with threaded portion on housing 34 to move gripper 32 up and down. Two guides 79, 81, both made of steel, are positioned on either side of lead screw 86 to ensure that gripper housing 34 moves up and down steadily.

Shield 100 serves to block undesirable particles from entering manipulator 18 and inhibiting its performance. Shield 100 can be made of any suitable material, but is preferably made of aluminum.

Cover 102, shown in FIGS. 1, 3, may be made of any suitable material but is preferably made of blow molded polyethylene, which is commonly known in the art. Cover 102 shields the working parts of container manipulating device 18 from dust and other particles which might otherwise interfere with the operation of the autosampler 10.

LEDS 104, 106, which are light-emitting diodes known in the art, are electrically connected to autosampler 10 and allow it to operate intelligently. Referring to FIG. 1, LED 104 is positioned above the furnace of parent instrument 12 and LED 106 is positioned on the opposite side of the ground plate 15. LED 104 and LED 106 cooperate with sensors positioned opposite each LED to allow the autosampler to determine, for example, if container 20 is in gripper fingers 40, 42, 44 or whether an error has occurred. LED 104 determines if autosampler 10 has a sample container 20 or a furnace lid 52 in its gripper fingers 40, 42, 44. LED 106 at the "zero position" allows autosampler 10 to determine if gripper fingers have released container 20 or if container 20 has mistakenly remained in its grip.

A method for handling and transferring specimen containers 20 generally follows the operation of autosampler 10 discussed above and comprises the following steps. First autosampler 10 is programmed by an operator and then specimen containers 20 containing specimens is loaded onto specimen trays 16, 16A. Specimen trays 16, 16A are loaded onto ground plate 15. See FIGS. 1, 2, 7.

Loaded trays 16, 16A are placed on ether side of autosampler 10 for sample pickup and remain stationary during operation of autosampler 10. Advantageously, the dual sample tray 16, 16A feature increases the sample throughput because one tray can be removed for reloading, for example, while the other is being used by autosampler 10.

Gripper 32 begins each session maximally vertically displaced; spool 36 is in the lower position and gripping fingers 40, 42, 44 are in the closed position; furnace lid 52 covers furnace access hole 26. FIGS. 1–4B. Manipulating device 18 is instructed by the operator via software to begin a session.

Before any specimens may be inserted into the furnace and before analysis of any specimens may begin, lid 52 must be removed from the furnace access hole. To do this, gripper 32 rotates via stepper motor 74 until it is directly above furnace lid 52. Gripper 32 descends via stepper motor 75 until it is near the top of the furnace lid 52. Heat, via a voltage source, for example, is then applied to wire 54 causing the temperature of the wire 54 to increase and further causing wire 54 to undergo a phase transformation. The phase transformation causes wire 54 to shrink, raising spool 36 from the lower position to the upper position and further causing gripper fingers 40, 42, 44 to move from the closed position to the open position. See FIGS. 4, 4A, 4B.

Referring to FIGS. 1–4B, gripper 32, with gripping fingers 40, 42, 44 in the open position, then descends via stepper motor 75 until it is in position to grasp lid 52. Fingers 40, 42, 44 close around lid 52 until the lip 53 of lid 52 fits snugly in recesses 72 of each bushings 66, 68, 70. Gripper 32 then ascends, raising lid 52 off the furnace access hole (FIG. 9); as gripper 32 passes LED 104, LED 104 and cooperating sensor confirm that gripper 32 has an object in its grasp and allows the operation to continue. Gripper 32 continues raising lid 52 until gripper 32 is maximally vertically displaced.

Gripper 32 then rotates via stepper motor 74 to transfer lid 52 to a point directly above a predetermined location. Then, gripper 32 descends via stepper motor 75 which drives lead screw 86; movement of lead screw 86 is guided by members 79, 81. Gripper 32 descends until lid 52 is placed firmly at its predetermined location. Heat is applied to wire 54 causing wire 54 to undergo a phase transformation and shrink, causing spool 36 to move from the lower position to the upper position, forcing gripping fingers 40, 42, 44 into the opened position thereby releasing lid 52. Gripping fingers 40, 42, 44 are then closed and gripper 32 is moved via stepper drive motor 75 until it is maximally vertically displaced. Gripper 32 is now ready to proceed with gripping and transporting a specimen container 20 to the furnace.

Manipulating device 18 then rotates about ground plate 15 until gripper 32 is positioned over the predetermined container 20. Motor 74 drives orbital gears 78, 80 about fixed gear 76 to rotate manipulating device 18.

When the gripper 32 is appropriately positioned over container 20, gripper 32 descends toward container 20. Heat, or voltage, is applied to shape memory metal wire 54. The voltage causes the temperature of shape memory metal 54 to rise, causing wire 54 to undergo a phase transformation. As a result, the wire 54 shrinks, forcing spool 36 to move from the lower position to the upper position moving fingers 40, 42, 44 from the closed position the open position. See FIGS. 3, 4, 4A, 4B. In the open position, the gripping fingers 40, 42, 44 are positioned loosely around the specimen container 20.

After the voltage is removed from the shape memory metal 54, spool 36 moves to its lowermost position by means of built up tension. As the spool 36 slides back, it causes gripping fingers 40, 42, 44 to move from the open position (FIG. 4B) to the closed position (FIGS. 3, 4), thereby gripping the specimen container 20.

After the container 20 is gripped, gripper 32 moves via stepper motor 75 in the manner discussed above until it is maximally vertically displaced. Then, gripper 32 rotates via stepper motor 74 in the manner discussed above until gripper 32 is adjacent to LED 106 in the "zero position." LED 106 determines that gripper 32 does in fact have container 20 in its grip and allows the operation to proceed. Gripper 32 then rotates via stepper motor 74 until it is positioned over the furnace access hole of the parent instrument 12. Gripper 32 then lowers specimen container 20 through the furnace access hole 26, 26A into the furnace and releases the container therein by applying heat to wire 54 in the same manner as discussed above. Gripper 52 then replaces lid 52 over the furnace access hole 26, 26A through operation of motors 74, 75 in the same manner discussed above.

After the appropriate test has been run, gripper 32 removes lid 52 and places it in its predetermined location. Then gripper 32 removes container 20 from the furnace of parent instrument 12 and rotates to the location of LED 106 (FIG. 1). LED 106 determines that specimen container 20 has indeed been removed from the furnace and is gripped by the gripper 32, then gripper 32 places container 20 in its predetermined location on tray 16. Gripper 32 then replaces the lid 52 over the furnace access hole.

Shape memory metal 54 activation is advantageous because a very precise amount of shrinkage takes place, depending on the composition of the metal 54, regardless of the amount of heat, or voltage, applied. Thus, it is impossible to overheat the metal 54 or to cause it to shrink more than desired. As a result, it is virtually impossible to over- or under-move spool 36, thus preventing any misplacement of container 20 or lid 52.

After autosampler 10 has been properly programmed and loaded, it advantageously operates without further human operator assistance. Further the autosampler 10 has the ability with the Pyris™ program, when properly programmed, to abort an analysis if problems occur with the transfer of a specimen container 20 and generates an error message which is displayed on the display screen of the host computer (not shown).

In its most preferred embodiment, autosampler 10 is capable of loading up to 45 samples without operator assistance, thus, freeing the operator to perform other tasks. Advantageously, because of the safety features built into the autosampler 10, the operator does not need to be in the vicinity of the autosampler 10 while it is working. Thus, the operator may load autosampler 10 near the end of the work day, and upon returning to work the next day, find the results of the analysis. As a result, autosampler 10 saves the operator much time and energy.

Autosampler 10 has numerous safety features. For example, autosampler 10 replaces the lid 52 (FIG. 9) between runs of each sample container 20. This feature prevents the furnace from receiving too much oxygen and it prevents foreign objects from falling into the furnace.

Figure 10:
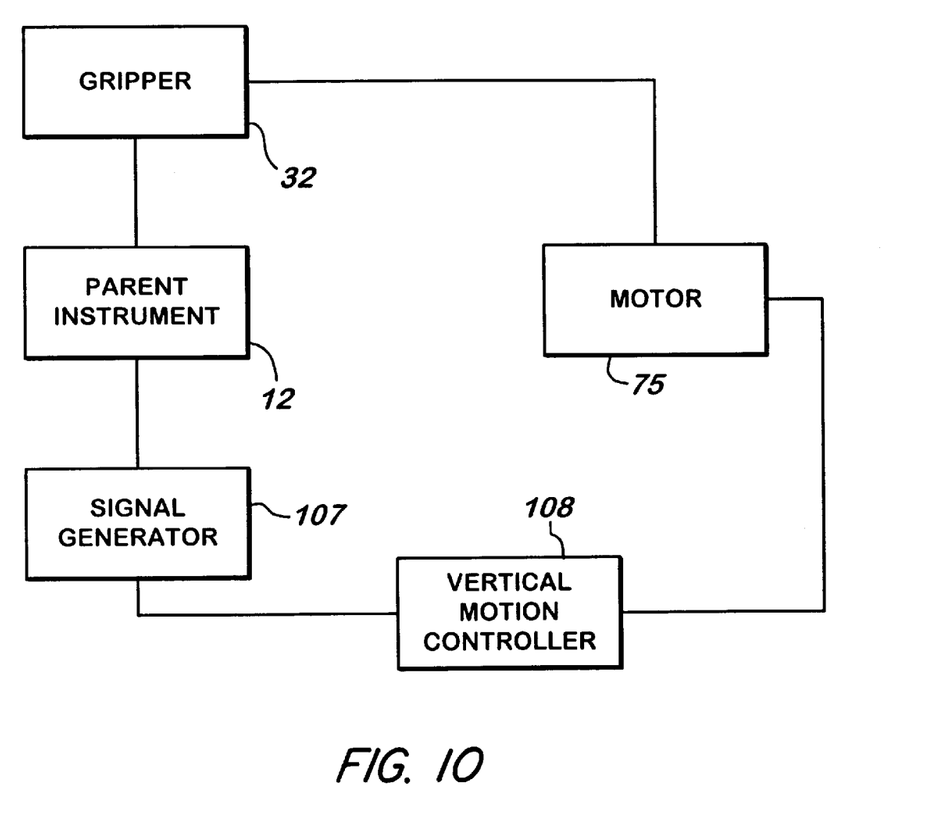
FIG. 10 is a block diagram of a feedback control loop of the gripping mechanism.

Referring to FIG. 10, autosampler 10 also comprises a feedback loop which accurately determines the location of container 20 relative to the location it is to be placed in parent instrument 12, such as the seat of the furnace, for example. In the preferred embodiment, an electrical signal is generated to tell gripper 32 the location of container 20 and when it is properly seated in the furnace. When container 20 is properly positioned, an appropriate signal is generated by a signal generator 107. The signal may be, for example, the weight signal from the balance when the parent instrument is a TGA or the sample temperature sensor signal when the parent instrument is a DSC. Signal generator 107 sends an appropriate electrical signal to vertical motion controller 108, which in turn sends an appropriate electrical signal to motor 75 to stop. When motor 75 turns off, downward movement of gripper 32 stops. This is advantageous over prior art instruments. The prior art instruments move a predetermined distance, such as ten centimeters; thus, if the prior art instrument is incorrectly calibrated, then the distance between the bottom of the sample container and its seat on the furnace, would be incorrect. This would cause the manipulating device to move an excessive amount or an insufficient amount; as a result, the container may fall from the device to furnace seat or drive the container into the seat of the furnace.

Advantageously, manipulating device 18 is connected to parent instrument 12 and all the necessary wiring to couple the two instruments together is internally contained. That is, the parent instrument comprises a housing, electronics positioned inside the housing and a connector for sending and receiving signals from the parent instrument electronics. The connector 22 of the manipulating device 18, when connected to the connector of the parent instrument 12, electrically connects the electronics of the parent instrument 12 with the electronics of the manipulating device. Because both connectors are internally contained and because the electronics for both instruments are internally contained, the autosampler 10 is very neat and attractive in appearance.

Further advantageously, manipulating device 18 is relatively small and light-weight. Still further, manipulating device 18 may be attached to parent instrument 12 without increasing the footprint of parent instrument 12.

FIG. 11 illustrates an autosampler 10A having an alternative gripper design, wherein two of the gripping fingers have been removed for clarity. Spring 110 is positioned inside gripper housing 34A such that it causes spool 36A to be in a normally lower position, as shown. When heat, such as voltage, is applied to memory metal wire 54A, it causes the temperature of wire 54A to rise. This increase in temperature causes wire 54A to undergo a phase transformation and shrink or constrict. When wire 54A constricts, it pulls spool 36A upward with sufficient force to compress spring 110 and move the gripping fingers 40A to an open position.

It should be understood that the foregoing is illustrative and not limiting and that obvious modifications may be made by those skilled in the art without departing from the spirit of the invention. Accordingly, reference should be made primarily to the accompanying claims, rather than the foregoing specification, to determine the scope of the invention.

What is claimed is:

1. An autosampler for manipulating a specimen container comprising:
   a ground plate;
   at least one specimen container tray removably fixed to the ground plate, the specimen container tray having a plurality of recesses for receiving a specimen container;
   a specimen container manipulating device, positioned on top of the ground plate and adjacent to the specimen container tray, comprising:
      a gripper comprising a gripper housing and a plurality of gripping fingers extending distally from the gripper housing and movable between an open and closed position, wherein in the closed position, the gripping fingers grip and hold a specimen container;
      shape memory metal positioned inside the gripper housing for controlling movement of the gripping fingers between the open and closed positions; and
      a heat source for applying heat to the shape memory metal, wherein when heat is applied to the shape memory metal, the temperature of the shape memory metal rises and the shape memory metal undergoes a phase transformation and constricts, causing the gripping fingers to move from the closed position to the open position.

2. The autosampler of claim 1, wherein the heat source comprises a voltage source.

3. The autosampler of claim 2, the gripper further comprising a movable member positioned inside the gripper housing and movable between an upper and lower position and connected to the shape memory metal, such that when the shape memory metal constricts, the movable member moves from the lower position to the upper position.

4. The autosampler of claim 3, wherein the movable member positions the gripping fingers substantially equidistantly from each other.

5. The autosampler of claim 4, the movable member comprising a spool positioned inside the gripper housing and movable between an upper and lower position, the spool having a top and a bottom and a bore extending therebetween and a recessed portion at the bottom thereof, a plurality of grooves substantially equidistantly spaced from each other, and, each gripping finger positioned in a groove of the spool.

6. The autosampler of claim 5, the gripper further comprising a rod positioned in the recessed portion of the spool.

7. The autosampler of claim 6 wherein the shape memory metal extends through the bore of the spool and around the rod.

8. The autosampler of claim 1 wherein the specimen container tray is stationary while the gripper manipulates the specimen container located thereon.

9. The autosampler of claim 1, the gripping fingers each comprising two ends, one end being closest to the specimen container, at least two of the fingers having bushings affixed at the end thereof closest to the specimen container.

10. The autosampler of claim 9, each bushing further comprising a recess sized and shaped to receive a lip of a furnace cover.

11. An apparatus for handling and moving a plurality of specimen containers comprising:

a ground plate;

at least one specimen container tray removably fixed to the ground plate, the specimen container tray having a plurality of recesses for receiving a specimen container;

a specimen container manipulating device, positioned on top of the ground plate and adjacent to the specimen container tray, comprising:

a gripper housing having an open end;

a spool positioned inside the gripper housing and movable between an upper and lower position, a plurality of grooves substantially equidistantly spaced from each other, a top and a bottom and a bore extending therebetween, and a recessed portion thereon;

a rod positioned in the recessed portion of the spool;

a plurality of gripping fingers, each gripping finger positioned in a groove of the spool and protruding from the open end of the gripper housing, the gripping fingers movable between an open and closed position for gripping and releasing a specimen container;

shape memory metal extending through the bore of the spool and around the rod; and a heat source for applying heat to the shape memory metal, wherein when heat is applied to the shape memory metal, the shape memory metal undergoes a phase transition and constricts causing the spool to move to the upper position which moves the gripping fingers into the open position.

12. The apparatus of claim 11 further comprising at least two specimen container trays.

13. The apparatus of claim 11 wherein the specimen container tray is stationary while the specimen container manipulating device manipulates a specimen container located thereon.

14. The apparatus of claim 13, the gripping fingers each further comprising two ends, one end being closest to the specimen container, at least two of the fingers having bushings affixed at the end thereof closest to the specimen container, each bushing having a recessed portion therein for receiving a lip of a lid of a furnace cover.

15. The apparatus of claim 11, the specimen container tray further comprising a bottom and at least one recess on the bottom thereof, the specimen container manipulating device further comprising at least one positioning pin sized and shaped to fit in the recess of the specimen container tray.

* * * * *